United States Patent [19]

Fleckenstein

[11] 4,161,437

[45] Jul. 17, 1979

[54] MEASURING PROBE FOR THE POLAROGRAPHIC DETERMINATION OF PARTIAL GAS PRESSURES

[75] Inventor: Wolfgang Fleckenstein, Kiel, Fed. Rep. of Germany

[73] Assignee: Drägerwerk Aktiengesellschaft, Fed. Rep. of Germany

[21] Appl. No.: 853,582

[22] Filed: Nov. 21, 1977

Related U.S. Application Data

[63] Continuation-in-part of Ser. No. 648,944.

[30] Foreign Application Priority Data

Jan. 15, 1975 [DE] Fed. Rep. of Germany ........ 2501399

[51] Int. Cl.² .............................................. G01N 27/46
[52] U.S. Cl. ................................. 204/195 P; 204/1 P
[58] Field of Search ................ 204/1 P, 1 T, 195 R, 204/195 P

[56] References Cited

U.S. PATENT DOCUMENTS

| | | | |
|---|---|---|---|
| 2,563,062 | 8/1951 | Perley | 204/195 G |
| 3,088,905 | 5/1963 | Glover | 204/195 P |
| 3,503,861 | 3/1970 | Volpe | 204/195 P |
| 3,530,046 | 9/1970 | Mochizuki et al. | 204/195 P |
| 3,912,614 | 10/1975 | Spracklen et al. | 204/195 P |

FOREIGN PATENT DOCUMENTS

667471  3/1952  United Kingdom ................ 204/195 G

*Primary Examiner*—T. Tung
*Attorney, Agent, or Firm*—McGlew and Tuttle

[57] ABSTRACT

The probe comprises a support of insulating or dielectric material, such as, for example, a glass tube drawn to a closed point at one end. An indicator electrode is supplied as a thin film of metal on the surface of the support, the metal being, for example, platinum or gold. An insulating sandwich-like multi-layer thin film is applied over the indicator electrode film. Preferably, a shielding electrode film is applied over the insulating sandwich-like film and is covered by another insulating film. A composite reference electrode film, including a layer of silver and a layer of platinum or gold, is applied over the outer insulating layer directly or separated by a film of water-proof material such as "TEFLON" and, for special purposes, the reference electrode film may be covered by another film of water-proof material. In the tip region of the probe, a cut surface is formed through the films and through the insulating support, which cut surface includes a cut surface of the indicator electrode forming the effective surface of the latter, the cut being made in a plane substantially perpendicular to the plane of the indicator electrode. The entire tip of the probe is coated with a diaphragm layer of a hydrophilic organic plastic polymer, such as cellulose acetate. The support structure may include two or even three glass tubes which are arranged in concentric radially spaced relation, with each tube carrying one or more of the several films. The films may be applied by cathode sputtering in vacuum deposition. Electrical conductors or leads are secured to the several electrodes and are preferably covered by the insulating or water-proof layers or films, the several films extending from the tip of the probe for a substantial distance along the support.

4 Claims, 13 Drawing Figures

100μ for a,b,c,d,e    10μ

MEASURING PROBE FOR THE POLAROGRAPHIC DETERMINATION OF PARTIAL GAS PRESSURES

CROSS-REFERENCE TO RELATED APPLICATION

This application is a continuation-in-part of application Ser. No. 648,944, filed Jan. 14, 1976, for "Measuring Probe for the Polarographic Determination of Partial Gas Pressures and Method of Making the Same, and now abandoned".

FIELD AND BACKGROUND OF THE INVENTION

The present invention relates to a measuring probe for the polarographic determination of partial gas pressures, in particular, partial oxygen pressure in aqueous solutions, particularly in biologic mediums, comprising an indicator electrode which, except for a very small effective surface, is insulated all around, a diaphragm protecting the effective surface against poisoning, and, if provided, a reference electrode.

Such measuring probes are used in medical and biological examinations if, for example, the partial oxygen pressure ($pO_2$) in the blood vessels, in the tissue, or even in individual cells is to be determined. The determination of the $pO_2$ makes it possible to draw conclusions about the metabolic activities or supply conditions in the live tissue.

The known oxygen measuring probes of this kind always comprise a central needle-shaped indicator electrode of platinum, gold, or the like, which is sealed in a glass insulator. The pointed tip of this needle-shaped indicator electrode lies bare as the effective surface of the indicator electrode and is protected against the organic medium by a plastic diaphragm, to prevent a poisoning of the indicator electrode or invalidation of the result, for example, by protein molecules. In most cases, the known measuring probes also comprise a reference electrode, frequently a silver electrode, which is usually also disposed at the tip of the probe, for example, as a tube fitted thereover.

In this kind of known measuring probes, substantially two basic types may be distinguished, namely, macroprobes, having a relatively thick insulating glass body and intended for measurements in blood vessels, and having a tip diameter of approximately 1 mm, with a central platinum wire having a thickness of some $10\mu$, and microprobes, which have a measuring tip so fine that they permit piercing individual cells of the tissue and determining the $pO_2$ thereof. The measuring electrode of a microprobe comprises a wire which is etched from some $10\mu$ down to a tip diameter of below $1\mu$, and the glass insulator has a diameter less than $0.1\mu$ in the tip zone so that a total diameter of approximately $1\mu$ is obtained at the tip of the probe. These microprobes also are coated with a plastic diaphragm.

During the measuring operation, measuring current is drawn from the indicator electrode, causing an afflux of oxygen molecules to be recharged at the effective surface of the measuring electrode. A high consumption of oxygen which, in this process, is unavoidable with measuring probes not covered by a diaphragm, leads to a stir effect and to an oxygen depletion in the area immediately adjacent the tip of the probe. Also, the oxygen consumption is related to the effective surface area and inversely dependent on the thickness of the diaphragm. Consequently, with a given effective surface, the diaphragm is provided as thick as possible. However, this strongly reduces the speed of response to the probe, depending on the solubility and rate of diffusion.

The solution to that dilemma might be a diminution of the effective surface but such a solution, however, meets with considerable difficulties. In microprobes, a diminution of the effective surface to a suitable small value results in too small diameters at the tip of the indicator electrode so that the mechanical stability thereof, which is determined by the platinum wire alone, is endangered. In macroprobes, up to date, thick diaphragms have always been used, and the disadvantage of a slow speed of response has been tolerated.

Known constructions of microprobes have still other drawbacks such as the great variation of the effective surface areas of the individual probes which, in the constructions of the prior art, is inevitable. Also, faultless glass sealings are very difficult to make. In most cases, during the manufacture, fine fissures or stresses occur in the glass insulator, which, later on, lead to cracks. Since every crack produces a new, additional, small effective surface, the parameters of such probes scatter considerably. Further, in such cases, the measuring surface is not confined to the tip but extends, in an uncontrollable manner, over a large surface of the shank adjacent the tip.

In addition, with very thin metal pins, as is the case with microprobes, it passes for a rule that glass sealings can be made only if the glass insulator is thinner than the metal pin. That is why microprobes with a satisfactorily small effective surface have always extremely thin glass insulations, the resistance of which to water, understandably, is unusually low, since they very rapidly become thoroughly hydrated. Thereby, the effective surface is enlarged, in an uncontrollable manner, to a multiple. Moreover, in such a case, as well as in the case of the formation of cracks, it is no longer possible to determine the spatial relationship between the measured value of oxygen and the measuring point.

SUMMARY OF THE INVENTION

The present invention is directed to measuring probes of the just-mentioned kind which assure a small consumption of oxygen while having a high speed of response and which are suitable for mass productions and for routine work.

In accordance with the invention, the indicator electrode is designed as a thin film of noble metal, or of an alloy having noble metal properties, which is disposed between an insulating support and an insulating layer, and the effective surface is formed by the exposed area of a cut end surface of the film included in a measuring surface of the probe formed by a cut surface extending substantially perpendicularly to the plane of the film.

In the inventive construction, instead of the indicator electrode being a wire sealed in a glass insulator, it is a thin film which is deposited on the surface of an insulating support. Even with very thick and thus stable supports, the deposited film, constituting the indicator electrode, can be made extremely thin and consequently the cross-sectional area of the film, which is situated, as the effective surface, in the measuring surface of the probe, can be extremely small. If, for example, such a thin layer has a thickness of $0.05\mu$, the order of magnitude of the effective surfaces of the smallest known probes is reached only with an extension in width of the film of approximately $20\mu$. By depositing such an electrode on a cylindrical support having a diameter of about 7μ, a probe is obtained which is, by orders of magnitude, mechanically more stable than any known microprobe having a platinum wire of 1μ in diameter. In addition, the thin-film technique, as known, for example, from the manufacture of electronic component parts, is so advanced that the thickness and conductivity of the thin-film electrode of the invention can be assured with an extreme accuracy and a very satisfactory reproducibility.

Further, in such a measuring probe, troublesome glass sealing is avoided, and the electrode film adheres always well to the surface of the support and does not tend to a formation of cracks or to other flaws, not even under rough handling and thermal influence. In addition, the mechanical resistance is higher, since the probe can be made thicker and a suitable strong material, such as glass, can be selected as the support.

Due to the distribution of the narrow effective surface over a more extended area, the stir effect is further reduced. For the first time, the inventive electrode offers the possibility, for example, of using a resistant probe suitable for piercing a stout biologic tissue, for measurements of rapid $pO_2$ variations in such a tissue.

Up to the present time, in pertinent discussions and publications on bio-electrodes, the oxygen indicator electrodes in microprobes and macroprobes have been classified on the basis of a tip diameter of 5μ. That is, from the point of view of the construction, below a diameter of 5μ, the mentioned drawbacks of the insufficient mechanical, electrical and chemical stability are always present. Thinner probes are also more suitable for point by point examination and are, with a given speed of response, less affected by the stir effect, while macroprobes are more stable, but less suitable for examinations with a high resolving power in space and time. Hitherto, in the manufacture and use of macroprobes and micro-measuring probes, it has been necessary to apply different methods and work with different devices.

A great advantage of the inventive probes is that they eliminate the mentioned differences between microprobes and macroprobes. A probe embodying the invention is to be classified, in accordance with the above definition, as a macroprobe having a high mechanical stability as well as constant measuring parameters, but also, in spite of that, the probe embodying the invention has a very high speed of response while, at the same time, it completely eliminates any stir effect.

Advantageously, the inventive measuring probe comprises a shielding electrode or layer which has the form of a thin metal film terminating closely adjacent to or in the measuring surface and is disposed on the insulating layer covering the indicator electrode, and which may be separated from the exterior and the measuring surface in an insulating manner. Such a shielding electrode prevents, for example, hum pickups. Known shielding electrodes could never be extended up to the immediate vicinity of the effective surface. This is possible for the first time in constructions in accordance with the present invention since, in the invention, the shielding electrode and the indicator electrode are designed as thin films and the shielding electrode is able to shield the indicator electrode up to the measuring surface. In addition, with the shielding electrode designed as a thin metal film, the diameter of the probe is increased to only a negligible extent. If it is desired to avoid a physical contact of the shielding electrode with the medium to be measured, a respective design can be chosen in which the shielding electrode is insulated relative to the measuring surface and the exterior.

A further advantageous provision of the invention is that the reference electrode is designed as a thin metal film disposed outwardly of, and insulated relative to, the inward electrodes of the measuring probe. This makes it possible again, aside from allowing the use of the same manufacturing technique for the indicator, shielding and reference electrodes, to extend the reference electrode up to the immediate vicinity of the measuring surface. For measurements in a biologic cell tissue, a small distance between the indicator electrode and the reference electrode is a great advantage since, in the biologic tissue, potential barries are present, for example, at the boundaries of organs or walls of cells, which, when situated between the two electrodes, may considerably invalidate the measuring results. Further, a small spacing of the two electrodes is necessary in order to keep the resistance in the measured medium between the two electrodes as low as possible. This is needed, for example, in cases where, for reasons of the measuring technique, a different potential is applied to the measured medium relative to that applied to the reference electrode. That is, in such cases, care must be taken to keep the resistance between the electrodes substantially lower than the resistance between the reference electrode and the connecting lead to the external potential. This situation is encountered always in cases where, with a grounded measured medium, the reference electrode is kept at the polarographic voltage while the indicator electrode is grounded through its precision resistor. This reference electrode may serve at the same time as a shielding electrode.

As a further advantage, the invention provides that the diaphragm covers the entire measuring surface, including the reference electrode. Thus, the effective surfaces of the indicator electrode and the reference electrode lie beneath the diaphragm, which diaphragm may be applied to the finished measuring tip of the measuring probe in a simple manner, for example, in a dipping bath. The electrodes come into contact with the examined medium through the diaphragm. In an alternative embodiment of the inventive measuring probe, the diaphragm covers the measuring surface except for the reference electrode, and the reference electrode is provided outside of the diaphragm, while extending over the measuring surface. In this embodiment, the measuring surface is covered by the diaphragm and, in addition, by the reference electrode which is provided at the outside of the diaphragm. This embodiment is characterized by a particularly strong resistance to diffusion of oxygen from the ambient medium to the indicator electrode. Such an arrangement, however, is possible only if the reference electrode is a thin film permitting a sufficiently rapid gas diffusion. This kind of probe provides a physical separation of the measuring chamber from the measured medium by means of the reference-electrode layer extending over the measuring surface. The measuring chamber is formed by the layer enclosed between the measuring surface and the reference electrode. This probe is particularly suitable for impulse polarography. Another advantage is the shielding of the diaphragm against foreign ions penetrating from the outside and affecting the chemical stability of the diaphragm and of the indicator electrode.

In a measuring probe for the determination of oxygen, the indicator electrode is made, advantageously, of gold or platinum and the reference electrode of platinum, silver, or gold. These substances are well suited for both polarographic measuring and for deposition in the form of a thin layer, by evaporation, cathode sputtering, or the like. For the impulse polarography of oxygen, gold is particularly suitable since, aside from the excellent properties for the formation of thin layers, it entrains an extremely slight slope of the polarographic plateau. In an alternative embodiment, the reference electrode may be formed by a platinum or gold layer and an overlying or underlying silver layer. Such a two-layer reference electrode, in which one of the layers is always a silver layer, is particularly suitable for impulse polarography because, due to the unequal frequency response at the passivation of platinum or gold, on the one hand, and silver, on the other hand, the two adjacent layers complement each other advantageously and the substantial portion of the current is carried, during the rise time of the pulse, by the platinum or gold layer and, in the course of the pulse duration, by the silver layer. With a chlorination of the silver layer, the adjacent platinum or gold layer assures the maintenance of a low layer resistance.

According to an advantageous development of the invention, the shielding electrode is made of aluminum or silicon and the insulating path between the shielding electrode and the measuring surface is formed by an aluminum or silicon oxide layer extending in alignment with the shielding electrode layer. Such a shielding electrode can be produced in a particularly simple manner. First, all layers of the measuring probe are deposited, one after the other. The shielding electrode also may be deposited, in the same thickness, up to the measuring surface. Then, in a simple oxidizing process, the front end of the shielding electrode is oxidized to a desired depth.

In an inventive probe for measuring hydrogen, the indicator electrode is made, advantageously, of palladium. Palladium is suitable for the polarographic determination of the partial hydrogen pressure.

In a further advantageous development of the invention, the insulating layers of the probe are designed as thin films terminating in the measuring surface. In such a case, i.e., if the insulating layers between the individual electrodes are also designed as thin films, the entire probe, with the possible exception of the diaphragm, can be manufactured while using the thin-film technique. All layers may be deposited, one after the other, in the same vacuum. Thereby, the manufacturing conditions become particularly clean and the probes can be manufactured, even in mass production, with extremely close tolerances. In addition, with the known thinfilm methods, one has an entirely free hand in the selection of the thicknesses and the materials of the insulating layers, particularly as compared to the known glass sealing methods. Further, with the thin layer structure of the invention, the directly superposed materials are allowed to have considerably different coefficients of expansion. This makes it possible, for the first time in the technology of polarographic microprobes, to select the materials solely by their electrical and chemical properties.

Advantageously, the insulating films are sandwich-like structures made of different, alternately superposed, insulating materials. Even through they are very thin, these insulating films have a high dielectric strength and high chemical stability. At the same time, advantageously the sandwich layers are designed, alone or in connection with adjacent metal layers, as traps for undesirable substances diffusing therethrough. In such thin layers, the speed of diffusion of harmful substances therethrough is extremely high. For layers which have been thoroughly hydrated by long use, oxygen, for example, is such a harmful substance. By providing sandwich layers placed on the other, possibly in connection with adjacent metal layers, as traps for such substances diffusing therethrough, these harmful substances can be intercepted very effectively in the sandwich layers or at a boundary between an insulating and a metal layer, so that they cannot penetrate up to the indicator electrode. Such a trap effect consists, for example, in the fact that the molecules diffusing through are chemically converted and bonded in a certain layer. At the same time, the voltages applied during the polarographic process may advantageously be used for supporting or inducing such an effect electrolytically.

Another advantageous development of the invention is that, through an impedance transformer controlled by the potential of the indicator electrode, the shielding electrode terminating before the measuring surface is kept at the potential of the indicator electrode. In the impulse method, self-capacitances due to the geometry of the probe may extend the effective $pO_2$ response time, because they change the shape of the impulse. Such capacitances occur particularly in microprobes in which the insulating dielectric between the measuring probe and the liquid, acting as a reference electrode, is very thin so that, up to the present, with this type of probes, impulse polarography, with a high $pO_2$ resolving power in time, has been impossible. Moreover, such capacitances vary with the depth of penetration of the probe into the measured medium so that, in practice, this again prevents attaining a high resolving power in impulse polarography.

If, in the "shifting shield" method, the shielding electrode, which is kept at the potential of the indicator electrode, is taken along, the capacitance between the indicator electrode and the shielding electrode, as well as leakage currents to the indicator electrode, are eliminated. However, the "shifting shield" method is particularly effective in cases where, as in the measuring probe of the invention, the shielding electrode shields the indicator electrode up to the foremost zone of the tip so that the residual capacitance of the measuring probe relative to the ambient liquid remains extremely low. Consequently, with the inventive arrangement, there can be measured, in the "shifting shield" method, pulses which are almost completely free from distortion through self-capacitances of the measuring probe. With this method of operation, the shielding electrode must be separated from the reference electrode.

It is further advantageous to give the measuring probe a circular cross-section. Such a design results in favorable strength factors and a small cross-section and, in addition, permits an inexpensive manufacture. Another advantage of such cylindrical measuring probes is the fact that they avoid problems with the lateral edges of the layers, which are absent in this design. Advantageously, in such measuring probes, the cross-section diminishes in the direction of the measuring surface. This results in a high mechanical resistance of the supported portion and in a fine tip. Advantageously, the support is a tube and the electrode and insulation layers are provided on the outside thereof. The manufacture of such probes has proven particularly simple since the drawing out of thin tubes, particularly of glass or the like, to very small diameters, such as needed for microprobes, may also be carried out in a vacuum, without problems.

In a further advantageous embodiment of the invention, the contact of the electrodes with connecting wires is established in a connection zone at the rear side of the measuring probe remote from the measuring surface. In this way, the connection zone is separated from the measuring zone of the probe. Consequently, the connecting wires are fixed in a thicker portion of the probe where enough space is available, while the tip of the probe can be designed with the desired small dimensions.

Advantageously, further supports are interposed between the electrodes in a manner such that their mutual spacing increases in the direction of the connection zone. In this manner, a structure is obtained in which a separate support is provided for each of the electrode layers. In the tip zone, the supports and layers converge to the desired small dimensions while, in the rearward direction, they diverge so that, in the connection zone, sufficient space is provided for the connecting wires to be fixed to the surfaces of contact of the individual electrodes deposited on the respective associated support. This results in a rugged construction in which the individual electrodes can be contacted in a particularly reliable and faultless manner. Another advantage is the satisfactory electric insulation by the respective supports of the individual electrode layers against each other. The substantial operational advantage is that disturbing leakage currents, through the layers covering the indicator electrode, can occur only in the short tip zone which is not protected by additional supports. The total leakage current which, in the known arrangements, may reach the order of magnitude of the measuring current, is thereby considerably reduced. If, for example, in a probe of the prior art, the current per surface unit is $10^6$ times smaller in the lateral surface of the probe than in the measuring surface, the resulting leakage current, at a surface ratio of $10^6:1$, will still be in the order of magnitude of the measuring current.

According to a further advantageous development of the invention, the additional supports are designed as concentric tubes tapering in the direction of the probe tip, and secured, in the zone of the tip, to the respective underlying layers and, in the connection zone, to each other. For this reason, glass or quartz glass advantageously are used as the material for the supports.

Since the individual metal and insulating layers of the measuring probe of the invention are very thin, their permeability to water is correspondingly high. Therefore, with increasing service time, there is a risk that the layers become destroyed by water or become conductive to such an extent that the desired insulating resistance is no longer assured. In addition, there is a risk that, upon penetration of oxygen and water up to the indicator electrode, the effective surface of this electrode will be enlarged to an uncontrollable extent. To solve this problem, the probe is coated laterally with a not easily swelling, and thus waterproof, plastic acting as an additional water barrier. This water barrier may be provided at the inside or outside of the reference electrode, depending on the required active surface of the reference electrode. If the measuring probe is used in impulse operation, the reference electrode may also be covered at the outside, for better protection since, in impulse operation, even a very small active area of the reference electrode situated in the measuring surface of the probe is sufficient.

In a particularly simple and economical embodiment of the invention, which is best suitable as a rugged macroprobe, the support or supports, extending in the rearward direction only slightly beyond the tip of the measuring probe, are embedded in a sealing compound which assures the retention of the probe on the testing apparatus. In this construction, the supports do not extend up to the mounting of the probe but extend only in the immediate vicinity of the tip, and are embedded in a sealing mass which, in turn, is cast integrally with the mounting of the testing apparatus. The connecting wires may also be embedded, in a well insulated manner, in the sealing compound.

Advantageously, the indicator electrode as well as, if provided, the shielding electrode, and the associated insulating layers are applied to the outside of the support which is designed as a tube open toward the measuring surface, the reference electrode is applied to the inside of the tube, the measuring surface as well as the aperture of the tube situated therein are covered with the well-hydratable diaphragm and with an overlying, non-hydratable, thicker diaphragm, and the interior of the tube is filled with an electrolyte. Measuring probes having an electrolyte chamber which is separated from the measured medium by the diaphragm and which directly adjoins the indicator electrode and the reference electrodes are known as macroprobes of the "Clark" type which are provided for determining oxygen. The main advantage of this type of probe is that a non-hydratable diaphragm can be used which has to be permeable only for oxygen. After being filled with the electrolyte, such a Clark-type probe is instantly ready for use. In general, with this type of probes, the measured values are more stable since the measuring space, i.e., the electrolyte chamber, is completely separated from the ambient medium.

A disadvantage of the known probes of this type is the minimum size of the effective surface of the indicator electrode, resulting from the construction. Consequently, a very thick diaphragm must be used in order to reduce the oxygen consumption to acceptable limits, which considerably increases the time of response to, typically, 15 seconds for 95% of the final value after an oxygen jump. An additional disadvantage is the variation of the measured values due to movements of the diaphragm relative to the electrodes upon pressure fluctuations. In the Clark-type probe, two parameters of the probe are determined by the mutual spacing of the diaphragm and the effective surface of the indicator electrode. These parameters are the oxygen diffusion between the diaphragm and the effective surface, through the electrolyte, and the cross-section of the electrolyte, which is important for the resistance polarization between the indicator electrode and the reference electrode. With a variation of the distance between the effective surface of the indicator electrode and the diaphragm, these two parameters vary in an uncontrollable manner and strongly invalidate the results of measurement.

In the Clark-type probe of the invention, the diaphragm, which is impervious to water, is firmly connected to the effective surface of the indicator electrode, through the thin, hydratable diaphragm. In consequence, variations of the oxygen diffusion path, which latter is given by the hydratable diaphragm, are avoided. In this design, the resistance polarization cannot vary either, since it is substantially determined by the constant resistance of the hydratable layer and is so small, due to the small effective surface of the indicator electrode, that it does not affect the results of the measurement. With the very small effective surface of the indicator electrode in accordance with the invention, the cross-section of the electrolyte chamber, and thus the overall cross-section of the probe, can be considerably reduced without causing a noticeable disturbing influence of the resistance polarization. This makes it possible for the first time to use the Clark-type electrode as a microprobe, while eliminating its drawbacks.

An advantageous method of manufacturing the measuring probe in accordance with the invention comprises the following steps:

(a) applying the electrode films and the insulating films to the surface of the support, by cathode sputtering in vacuo;

(b) forming an exposed measuring surface by a cut through the applied layers; and (c) applying the diaphragm to the measuring surface.

By vacuum deposition, very pure layers can be obtained, which are applied to the surface of the support without any impurity. At the same time, cathode sputtering offers the advantage of very well adhering layers. Following the deposition of the layers, a cut surface is produced laying bare all of the applied layers, and this surface serves as the measuring surface of the probe. Thereupon, the diaphragm is applied. In one advantageous variant of the method, the cut surface is produced by breaking and/or grinding off the respective portion of the support or, should the inaccuracy of this step be disturbing with very thin probes, the cut surface is produced by etching the layers in a chemical way or by ion or electron beam erosion or abrasion. The ion beam method is quite particularly suitable for producing an exactly defined measuring surface, due to the fidelity of removal by means of masks. An additional advantage of this method is the possibility of carrying out this operation, which is sequential to the deposition of the layers, in the same vacuum, which further reduces the risk of contamination.

Advantageously, the supports are heated in a vacuum and drawn therein into the desired shape, prior to applying the layers. This may be done in the same vacuum so that the layers are deposited on a freshly drawn and thus very pure surface of the support.

A further advantage of the method is that, at the rear ends of the electordes, each of the surface areas needed for establishing the contact is masked, during the application of the overying layers, by screening the finished electrode film against a spot-like cathode sputtering source which is bombarded by a focused ion beam. With a suitably high vacuum, a spot-like cathode sputtering source may serve as a source of a straight path atomic radiation. Therefore, the surface area needed for establishing contacts may be screened in an appropriate manner, by interposed masks, during the deposition of the overlaying layers, so that they lie bare for purposes of further contacting.

The method is also advantageous in cases where the probe is provided with a shielding electrode of aluminum or silicon. In such a case, in accordance with the invention, upon applying all layers and laying bare the measuring surface, the layer of the shielding electrode, from the measuring surface up to a desired insulating depth, is oxidized by electrolytic oxidation in a liquid, solid, or gaseous electrolyte. In this way, the necessary insulating layer between the shielding electrode and the measuring surface is produced in a particularly simple and very accurate manner. A particularly advantageous process is anodization by means of a gaseous electrolyte which, for example, is produced in a glow discharge. The particular advantage is the possibility of carrying out this process again in vacuo, following the preceding operational steps, so that contamination is avoided. With a suitable selection of the substances for the other layers, these layers will not be attacked.

For the deposit of the layers on cylindrical supports, the layers are applied to the outside of the support advantageously so that the support is rotated about its own axis, as a planet axis, while this axis revolves in a planetary motion about a sun axis passing through the sputtering source, the angular position of the planet axis relative to the sun axis being adjustable. The rotation of the support about its own axis assures a uniform deposition of the layer on the entire surface of the support, while the planet-like revolving about the sun axis compensates for the irregular radiation from the sputtering source in different directions. Consequently, a plurality of supports may be positioned in a circle simultaneously, without any risk of producing unequally thick layers.

The angular adjustability of the planet axis relative to the sun axis permits adjusting of the support with respect to the sputtering source at different angles, whereby the speed of deposition of the layer may be controlled. This angular adjustability is particularly advantageous for depositing the reference electrode in cases where the reference electrode extends over the entire measuring surface. With unequal angular positions of the measuring surface and the lateral surface of the probe relative to the sputtering source, unequally thick layers of the reference electrode can be deposited on these two surfaces.

For applying a reference-electrode layer to the inside of the tubular support of a measuring probe of the Clark type, it is advantageously provided that a metal pin, furnishing the sputtering material and having a diameter substantially corresponding to the inside diameter of the tubular support, is tapered, in the direction of the tip, more steeply than the interior surface of the tubular support, and positioned within the support so that its tip is flush with the front aperture of the tube. During the cathode sputtering operation, the pin is bombarded, in this position and through the aperture, with ions. The penetration of metal atoms knocked out by cathode sputtering into the interior of a very narrow tube raises considerable problems. In addition, they penetrate, to an only very small depth. Therefore, with conventional sputtering techniques, a complete inside coating of a very narrow tube having an inside diameter of 10 to $100\mu$ is not possible, the more so as the tube is pointed. The method of the invention, however, avoids such drawbacks by providing that the cathode to be sputtered, and which is accommodated in the interior of the tube, has a suitable shape adapted to the inside shape of the tube. According to this provision, the free space between the surface of the cathode and the inside surface of the tube widens, in spite of the tapering surface of the tube, in the direction of the tube end so that, therefrom, the ions causing the sputtering can enter in a satisfactory manner. This method results in a uniform coating of the interior of the tube up to a depth which cannot be reached with a conventional sputtering technique.

A relatively simple method of manufacturing measuring probes having a plurality of supports, each associated with an electrode layer, which is suitable also for mass production, comprises the following steps:

(a) applying an indicator-electrode layer as well as one or several insulating layers to the innermost support and contacting the indicator electrode in the connection zone;

(b) fitting a support tube, which has been drawn out to the desired shape and cut off at a location having a suitable diameter, over this arrangement until the tip of the arrangement protrudes therefrom, fixing the front rim of the cut end of this tube in a manner impermeable to liquids, applying the second electrode layer as well as an overlying insulating layer to this arrangement, and contacting this electrode layer; and (c) fitting another support tube thereover and fixing, coating and contacting this tube.

Thus, in this method, first, the respective inside support is coated and contacted by a current lead. Thereupon, the next outside support tube is fitted thereover and the next layers are applied to this second support tube as well as, in the tip zone of the probe, to the layers which are already deposited on the inside support. The breaking off of the support tube and fitting over the already finished arrangement including the underlying layers and supports, as well as the subsequent fixing of the newly fitted support tube by means of a glass solder or the like, are relatively simple operations which assure a satisfactory reproducibility of the parameters of the probe, in spite of the complex and heterogeneous structure of the probe. In particular, the tip of the probe, which is most important for the parameters of the probe, remains unaffected by these operations which take place in a more rearward portion of the probe.

In this method, it is advantageous to secure the respective connecting wire or lead to the support before mounting the support in the probe so that, during the subsequent application of the electrode layer, the wire is also coated with this layer. Due to this provision, a well conducting contact is assured between the electrode layer and the connecting wire.

An object of the invention is to provide an improved measuring probe, for the polarographic determination of partial gas pressures, and an improved method of making the same.

Another object of the invention is to provide such a measuring probe which assures a small consumption of oxygen while having a high speed or response.

A further object of the invention is to provide such a measuring probe and a method of making the same which are suitable for mass production and for routine work.

For an understanding of the principles of the invention, reference is made to the following description of typical embodiments thereof as illustrated in the accompanying drawings. dr

DESCRIPTION OF THE PREFERRED EMBODIMENTS

Figures 1, 4:
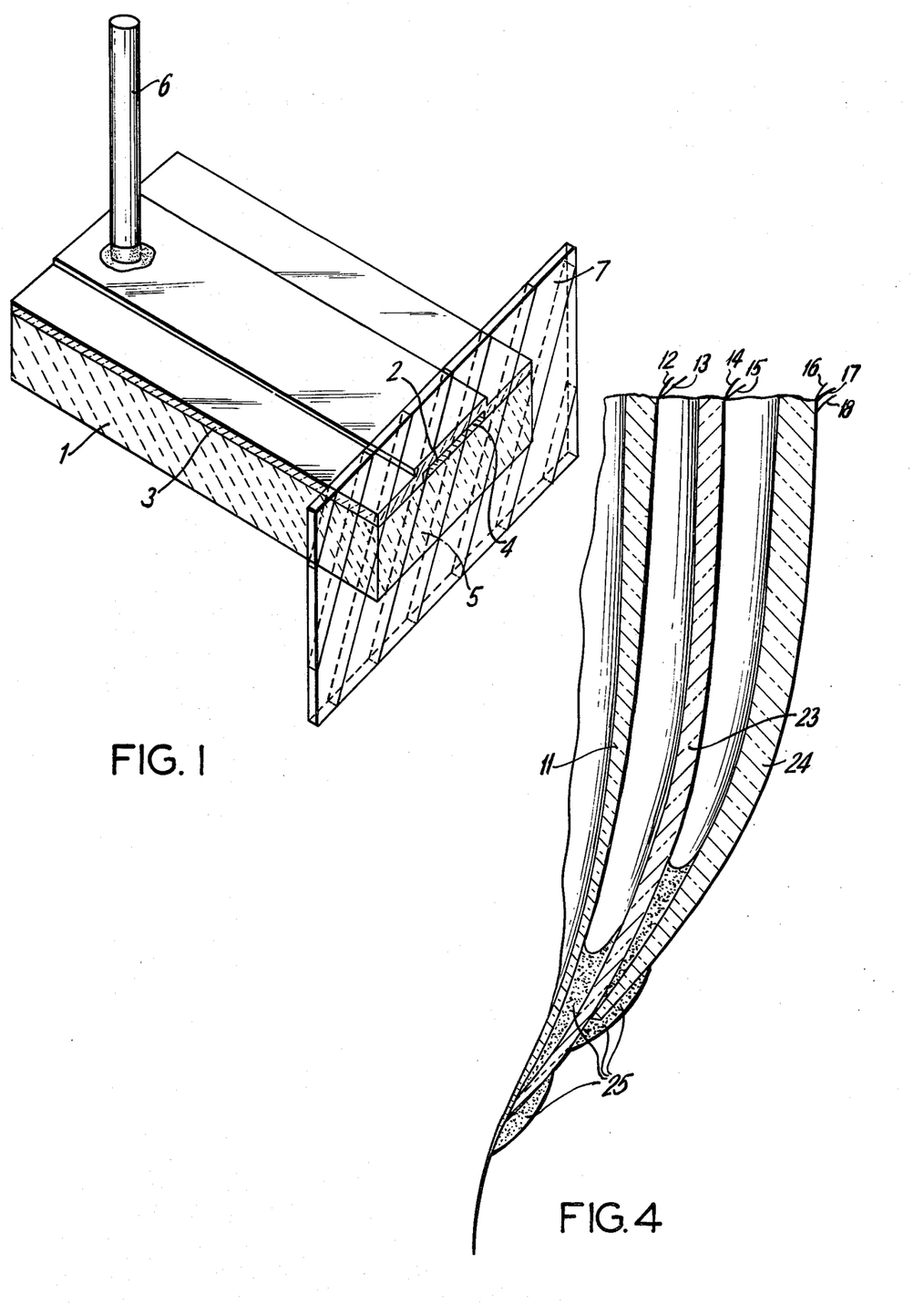
FIG. 1 is a perspective view of a simple embodiment of the inventive probe comprising a plate-shaped support.
FIG. 4 is an enlarged view of the detail IV of FIG. 2.

FIG. 1 shows a probe embodying the invention and comprising a plate-shaped support 1 which, for reasons of mechanical resistance and insulation, is made of a ceramic material, glass, quartz glass or the like. The support may also be an insulated metal pin (not shown) usable as a reference electrode. On the surface of the support plate, an indicator electrode 2 is provided. It comprises a thin film of a substance which is suitable for the respective polarographic purpose, for example, of platinum or gold, if an oxygen electrode is concerned. The design of the electrode in the form of a thin film involves the use of one of the known thin film techniques, such as evaporation or cathode sputtering. In accordance with the invention, however, the indicator electrode is applied by cathode sputtering since this method results in a particularly good adhesion on the support plate which is of particular importance for the present application.

On the top of indicator-electrode film 2 and the remaining surface of support plate 1, an insulating layer 3 is provided insulating the indicator electrode against the measured medium, for example, an aqueous solution, blood, or the like. In accordance with the invention, the insulating layer is also applied in the form of a thin film, by cathode sputtering. Here, the cathode sputtering method has again the advantage of a very satisfactory adhesion and a further advantage of making possible a free choice of resistant materials having a high dielectric strength.

In the illustrated example, the indicator electrode is designed as a narrow strip which is covered, up to the lateral edges of plate 1, with insulating layer 3. The effective surface 4 of indicator electrode 2 terminates in a measuring surface 5 of the probe, extending transversely to the plane of the layer. At a location remote from measuring surface 5 of the probe, indicator electrode 2 is contacted with a connecting wire 6 which is passed through insulating layer 3 and establishes a connection to the polarographic measuring equipment.

Measuring surface 5 is covered with a diagrammatically indicated diaphragm 7 which, in practice, may be applied by dipping the tip of the probe, including measuring surface 5, into a solution containing the diaphragm material which is a hydrophilic organic plastic polymer such as cellulose acetate, and subsequent drying or the like. Diaphragm 7 particularly covers the effective surface 4. In an oxygen measuring probe, the diaphragm must be permeable to oxygen, water and OH ions since, during the measuring operation, oxygen penetrates to the effective surface and is there reduced to OH ions, with consumption of water. On the other hand, the diaphragm has to be impermeable to poisoning ions and molecules.

Since the indicator electrode is designed as a thin film, it can be deposited, in a well reproducible manner, in thicknesses within the range of some hundredths to several tenths of a $\mu$. Therefore, even with a greater width of the indicator electrode film, which is kept constant during the application by masking, shading, or the like, the effective surface 4 can be very small, with an easily and very accurately reproducible area in the range of $1\mu^2$. At the same time, however, as may be seen in FIG. 1, support plate 1 can be very wide and thick and thus have a high mechanical stability. With the same, extremely small, effective surface 4, the inventive microprobe or macroprobes differ from each other only by the thickness and width of support plate 1.

What cannot be seen in FIG. 1 is that, preferably, insulating layer 3 is a sandwich layer comprising a plurality of superposed layers of extremely small thickness and having, due to this structure, a particularly high dielectric strength. On its exterior, i.e., toward the aqueous medium, insulating layer 3 may be covered with an additional plastic layer impermeable to water (not shown in FIG. 1) but care must be taken during the application of such a layer, for example, in an immersion bath such as in the case of diaphragm 7, not to cover measuring surface 5 with this waterproof diaphragm.

Figure 2:
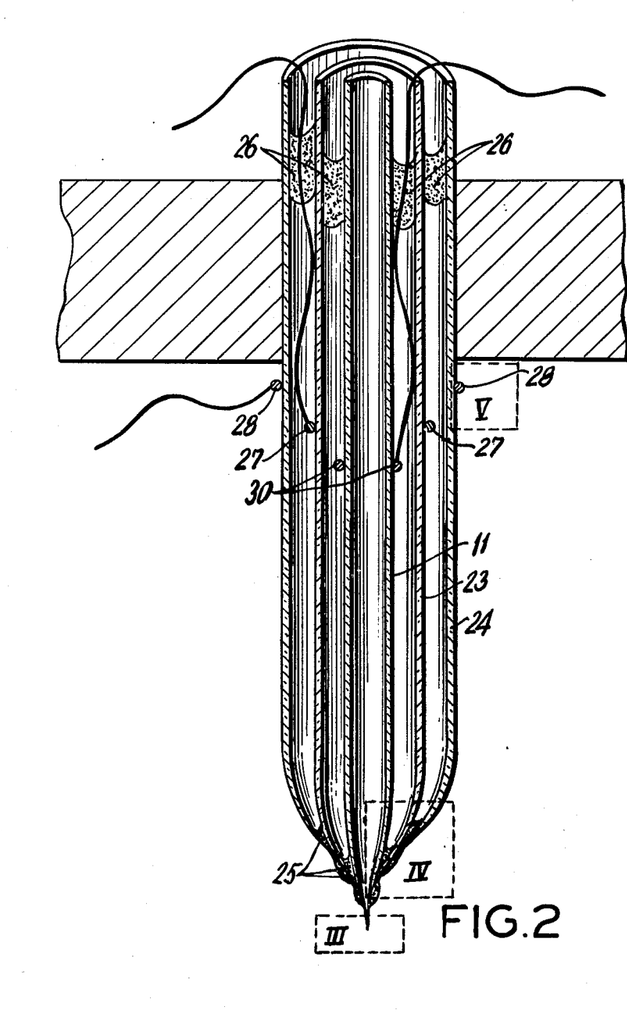
FIG. 2 is a sectional view of an embodiment of the inventive measuring probe comprising three coaxial hollow supports.
Figure 3:
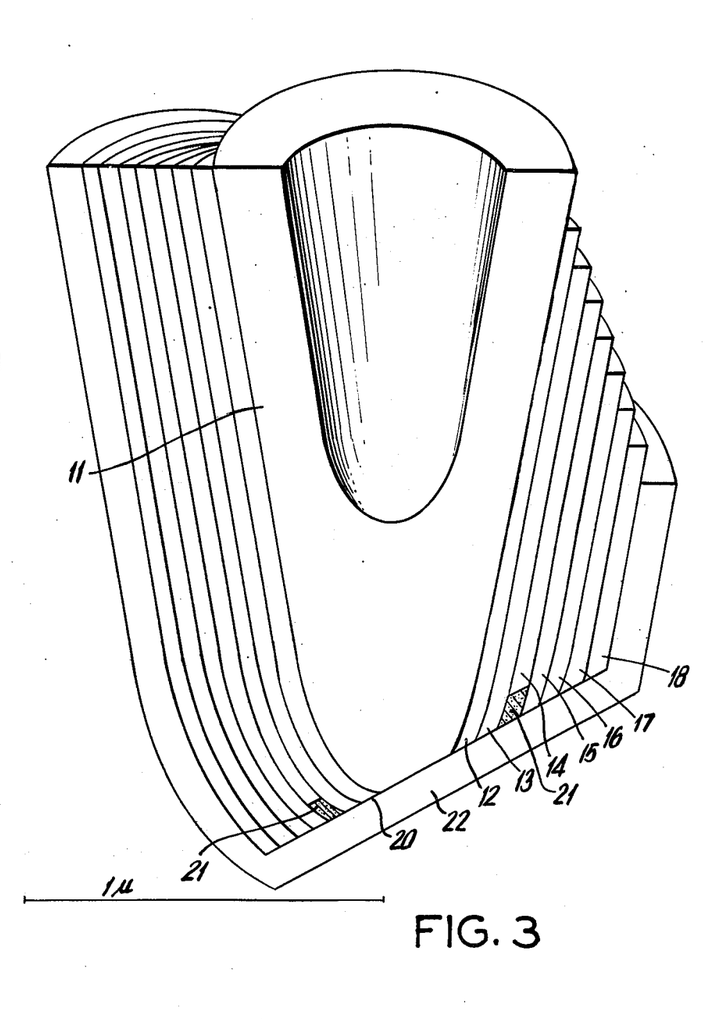
FIG. 3 is a greatly enlarged view of the detail III of FIG. 2.
Figure 5:
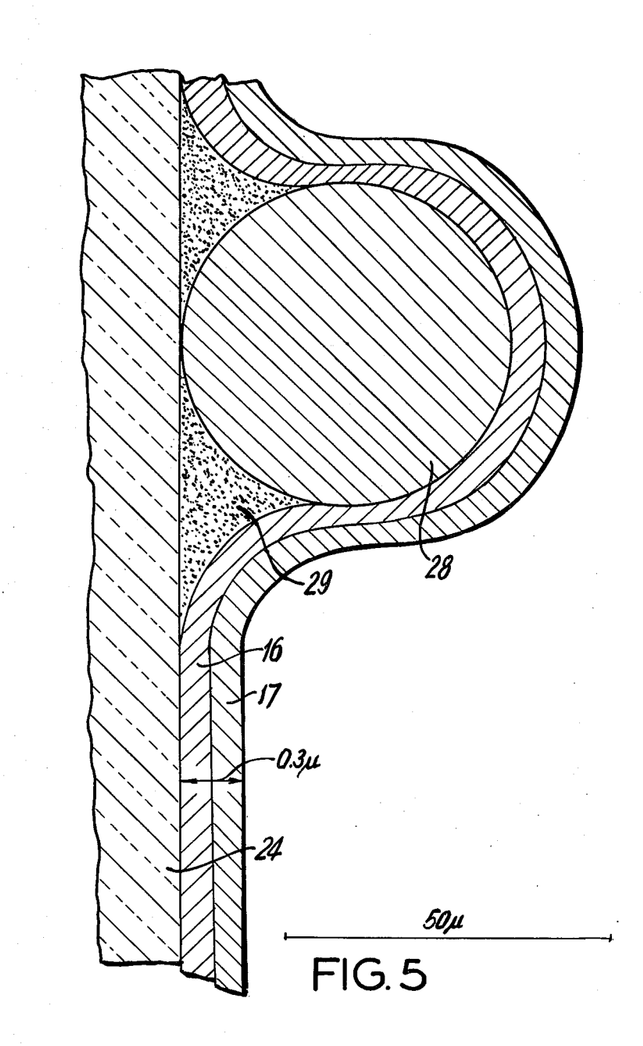
FIG. 5 is an enlarged view of the detail V of FIG. 2.

FIGS. 2 to 5 show another embodiment of the inventive measuring probe. FIGS. 3 to 5 are enlargements of details of FIG. 2 which cannot be shown in another way since their dimensions differ by about four orders of magnitude. In the respective figures, scales are indicated to illustrate the order of size.

First, FIG. 3, showing a sectional view of the tip zone of the probe, will be discussed. For clarity, hatching or sectioning has been omitted. Also, the layers are shown in a simplified manner, with equal thicknesses. Actually, depending on the purpose and used material, the thicknesses differ from each other, but within the indicated order of magnitude.

In the present example, the tip of the probe has a diameter of approximately $1\mu$ so that this probe may be used as a typical microprobe for determining oxygen, for example, in the individual cells of a biological tissue. With these dimensions, the tip is so fine that, in the representation of FIG. 2, it would no longer be optically perceptible.

The support is a cylindrical glass tube 11 which is tapered in the direction of the tip and closed on the tip end, and to the outside surface of which a plurality of overlying layers is applied. In sequence from the inside to the outside, these layers are an indicator electrode film 12 which, in the case of an oxygen measuring probe, such as shown in the figures, is made, for example, of platinum or gold. The following layers are an insulating sandwich film 13 and a shielding electrode film 14. As may be seen in FIG. 3, with this thin film structure, the shielding electrode covers indicator electrode 12 very exactly up to the tip of the probe. Therefore, field straying to the indicator electrode can be eliminated almost completely or, in the "shifting shield" arrangement, with shielding electrode 14 traveling along at the potential of indicator electrode 12, the capacitance of the indicator electrode relative to the ambience, which is disturbing in impulse polarography and which, with such a small size of the layers and, particularly, with such thin insulating layers, is very high, can be eliminated.

Shielding electrode film 14 is followed by another insulating film 15. To insulating film 15, there is applied a two-layer reference electrode comprising two thin metal films of which one, in the showing of FIG. 3 the inner one, is a platinum film 17 and the other is a silver film 18. These two films forming the reference electrode complement themselves advantageously since, with the silver film chlorinated through after longer use, platinum film 17 remains well conducting up to the location of contact and since the two films which, in impulse polarography, have a different frequency response, improve the pulse fidelity of the arrangement at different points of the impulse.

Between platinum film 17 and insulating film 15, a water-proof layer 16, for example, of "TEFLON" or the like, is deposited, presenting a lateral penetration of water into the underlying layers or films. This layer or film may be applied either by cathode sputtering, as are the other films, or, for reasons of simplicity, by dipping the tip, finished up to layer 15, into a bath containing the dissolved layer or film material.

On the tip of the probe, the end portion of the arrangement comprising support tube 11 and layers 12 to 18 applied thereto is ground off in a plane extending substantially perpendicularly to the axis of the probe and through all of the layers and the point of the support tube, or they are broken off or removed by another method so that all of the layers open with their thus exposed front faces or edges to this plane forming the measuring surface 19. The exposed face of indicator electrode 12 forms the effective surface 20. Shielding electrode layer 14 must be insulated relative to measuring surface 19 in order to perform its function. In this embodiment, in accordance with the invention, shielding electrode 14 is formed of an aluminum or silicon film the tip end portion 21 of which is oxidized from the exposed measuring surface 19 up to a predetermined depth. This oxidized portion of shielding layer 14 insulates the layer relative to measuring surface 19.

The entire tip of the probe is coated with a diaphragm layer 22 which, for reasons of simple manufacture, covers not only measuring surface 19, where it is actually needed, but the whole tip. Advantageously, again, this layer, like diaphragm layer 7, is produced by immersion.

Returning now to FIG. 2, this shows that, aside from the first, central glass support tube 11, the probe comprises two further glass support tubes 23 and 24 which are concentric with the first tube 11. Substantially, the tubes are of mutually equal overall length of several centimeters and have diameters in the range of several millimeters. Central support tube 11 is drawn out from its initial tube diameter of about 2 mm to a thin tip, shown in FIG. 3, and having a diameter less than 1μ and is closed at its tip end.

The outer support tubes 23 and 24 are also thinly drawn out and cut off at an inside diameter of the order of 100μ. At a location where the outside diameter of central support tube 11 has approximately this dimension, i.e., of some 100μ, inwardly of measuring surface 19 of the probe, outer support tubes 23 and 24 are connected to each other and to tube 11 in a manner impermeable to water, by a sealing compound 25, or by glass solder or the like. In addition, at their rear or outer ends, the support tubes are firmly connected to each other by a sealing compound 26. The rear end of outer support tube 24 is clamped in a suitable mounting of the probe, indicated in FIG. 2. The manner of supporting the mounting of the probe depends on the respective specific application.

In FIGS. 2 and 4, the thin films shown in FIG. 3, are not representable, for dimensional reasons. The distribution of these layers, which are not visible with the naked eye, is indicated in FIG. 4 at the upper, broken-off ends of the support tubes.

Indicator electrode layer 12 and associated layer 13 are provided throughout on central support 11. Shielding electrode layer 14, associated insulating layer 15 and the water checking layer 16 are deposited after support 23 has been fixed. Thus, in the tip zone, these layers repose on insulating layer 13 and then extend over the sealing compound fixing tube 23 and over tube 23 up to the upper zone thereof. Upon fitting the outermost support tube 24, reference electrode layers 16 and 17 are applied thereto thus covering, in the tip zone, the underlying layers, then the sealing compound fixing tube 24 and, further, tube 24 up to the upper zone thereof. Diaphragm 22 covering the tip all over is provided only in the tip zone and does not extend necessarily up to outer support tube 24.

At the rear or outer end of the probe, connecting wires 30, 27 and 28 are provided for the indicator electrode, the shielding electrode and the reference electrode, respectively. In each case, as shown in FIG. 5, they are secured to the outer surface of the support by means of glass solder 29, prior to applying the respective layers, and then coated with the respective electrode layer which extends at least up to the connection zone.

As is evident from the comparison of the different figures, in the by far largest area of their extent, the electrode layers are separated from each other and from the medium surrounding the probe by the very large radial spacing of the supports, which are closed in a watertight manner at their opposite ends by a sealing compound and thus have a highly insulating effect. In addition, as may be seen in FIG. 2, the contact zone of the individual electrode films is provided far away from the tip zone and the connecting wires for the indicator electrode and the shielding electrode extend in the interior of the probe, i.e, are well protected and highly insulated.

Because of the small measuring currents which are of the order of up to $10^{-12}$ amperes, probes are extremely sensitive to leakage currents. The inventive probe illustrated in FIGS. 2 to 5, however, prevents such leakage currents along the largest part of its length due to the great insulation distances between the electrodes deposited on different support tubes.

In the tip zone, the leakage currents can also be completely eliminated by using the "shifting shield" technique. Upon applying the potential of the indicator electrode to the shielding electrode through an amplifier having a low output resistance, the voltage difference between these two electrodes and, thereby, any leak current are eliminated. In this way, leakage currents can be reduced by orders of magnitude more than by insulation measures. If a "shifting shield" method is used, the necessary insulating layers between the electrodes may be relatively thin.

Figure 6A:
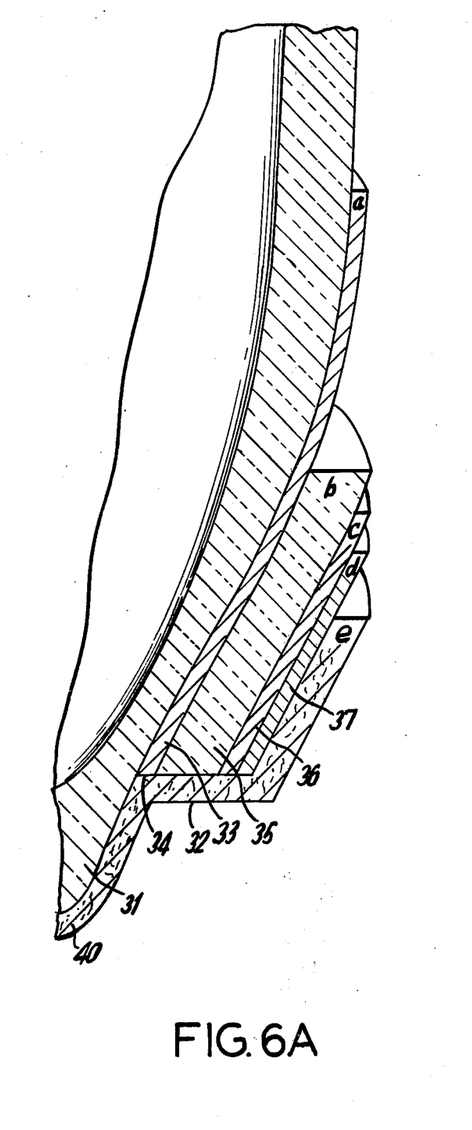
FIGS. 6A and 6B are enlarged sectional views of the detail VI of FIG. 7, taken through the tip of another embodiment of the inventive probe comprising a relatively thick support (macroprobe), the left (6A) and righthand (6B) portions with respect to the center line being shown in different designs in accordance with different manufacturing methods.
Figure 6B:
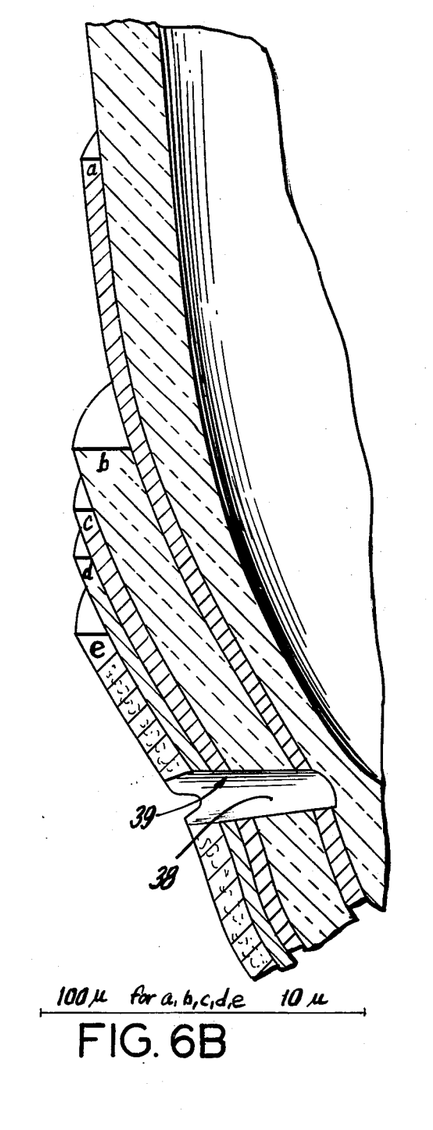

FIG. 6 shows another embodiment of the inventive probe which is particularly rugged in construction, has a long life, and is easy to manufacture. However, in its tip zone, this support tube is thicker by one to two orders of magnitude (see the scales) than the support tube shown in FIG. 3. In this arrangement, the measuring surface 32 is offset rearwardly or outwardly relative to the tip of support tube 31, to a location where the support tube has a wall thickness in the order of magnitude of 10μ and an outside diameter in the order of magnitude of 100μ. Due to limitations of drawing possibilities, in FIG. 6, these differences in thickness are only indicated. Support tube 31 carries an indicator electrode film 33 having approximately the same thickness as indicator electrode film 12 of the embodiment of FIG. 3. Consequently, in spite of the large diameter of support tube 31 at the location of the measuring surface, the effective surface 34 of indicator electrode 33 is very small.

For example, with a diameter of the annular effective surface of 50μ and a layer thickness of 0.2μ, the area of the effective surface is only 30μ². Thus, this construction combines the advantage of a high mechanical stability of the probe tip with the advantages of a very small stir effect, relative to the thickness of the diaphragm, because the narrow effective surface is distributed over a relatively large annular area.

An insulating film 35 which, for example, comprises a sandwich arrangement of $Al_2O_3$ and $SiO_2$ layers and which, in this construction, is considerably thicker than the insulating films of the embodiment of FIG. 3, is deposited on indicator electrode film 33. This film has a thickness, for example, of some 10μ. With such a thickness of the insulating film, a reliable insulation of the indicator electrode is maintained even for a long service time. On insulating film 35, a two-layer reference electrode is provided comprising a gold layer 36 and a silver layer 37.

Measuring surface 32 of this probe is not flush with the tip of support tube 31. This results in advantages for the service life of the films since, for the most part, mechanical stresses of the probe tip are absorbed by the tip of the support itself without mechanically stressing the effective surface. In this arrangement, however, the measuring surface is to be produced otherwise.

For example, in the embodiment shown in FIG. 6A, the effective surface may be produced, after all of the layers have been applied, by dipping the probe tip into an etching bath which removes the layers applied to the support up to the effective surface. A preferred process, however, is ion beam abrasion which makes it possible, upon masking the layer portions above the effective surface, or providing a screen in this zone, to remove the layer portions below the effective area while producing a neat cut edge.

In FIG. 6B, another design of the probe tip is shown in which the support has the same shape and sequence of layers. However, the effective surface is produced by another process, namely, electron beam erosion. In this embodiment, by means of a finely focused electron beam, a groove 38 is milled extending up to support 31 and forming, by its upper face 39, the effective surface of this kind of probe. The layer portions remaining below groove 36 down to the probe tip are inactive since they are completely separated from the main parts of the layers by the groove circularly surrounding the probe. Because this lower portion of the layers does not disturb at all, they may be left on the probe.

After producing an effective surface 32 or 39, the probe tip of both embodiments, FIGS. 6A and 6B, is coated with a diaphragm layer 40, preferably in an immersion process.

Figure 7:
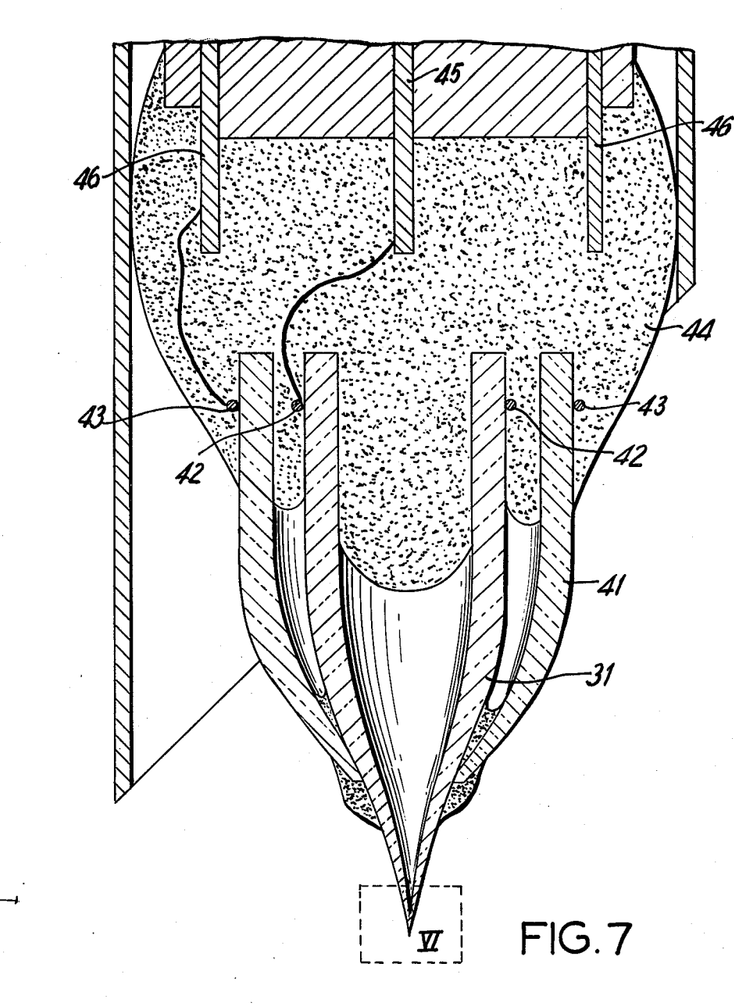
FIG. 7 is a sectional view of the entire probe comprising a tip in accordance with FIGS. 6A and 6B.

The upper part of this kind of probes, which is identical for both of the tip designs in FIGS. 6A and 6B, is shown in FIG. 7. Adjacent the immediate tip zone of the probe, thus at a distance of some 100μ, this probe is provided with a second, outer, support tube 41 which is designed in the same manner as support tube 23 of the embodiment according to FIGS. 2 to 5 and secured to inner support tube 31. In this probe again, indicator electrode film 33 and the associated insulating film 35 are provided on inner tube 31 and extend over the connection point to outer tube 41, while reference electrode films 36, 37 extend, first, in the tip zone, on insulating film 35, and then, over second tube 41. Connecting wires 42 and 43 for indicator electrode layer 33 and reference electrode layers 36 and 37 are again secured to the surface of the support tubes prior to the application of the layers and then coated with the respective electrode layers as has been explained in connection with FIGS. 2 and 5. In this probe, a third support tube is absent since there are only two electrodes, namely, the indicator electrode 33 and the reference electrode 36, 37, while a shielding electrode is not provided in this simpler design.

However, this embodiment may also be provided, in addition, with a shielding electrode which, of course, requires again a design with three support tubes.

Immediately inwardly of the probe tip, closely adjacent the zone where they are connected to each other, support tubes 31 and 41 are cut off. The probe tip thus obtained is embedded in a body 44 of sealing compound in which also the connecting wires 42 and 43 extend and are connected, within the sealing body, to the middle wire 45 and shield wire 46 of a coaxial shield cable. Sealing body 44 secures the probe to the cable serving as a mounting means for the probe.

This design of the probe simplifies the manufacture and results in a high mechanical resistance due to the sealing compound body engaging or surrounding all parts of the probe and assuring to a high extent the electric insulation of the outer portions of the electrodes and of the connecting wires. The probe shown in FIG. 7, in a size indicated by the scale, serves for examinations during which it is stuck in only by its tip. Another probe, however, the diameter of which would be reduced in the connection zone by approximately the factor 10, may be designed for being advanced within the cannula indicated in the figure and for being stuck in deeper regions.

Figure 8:
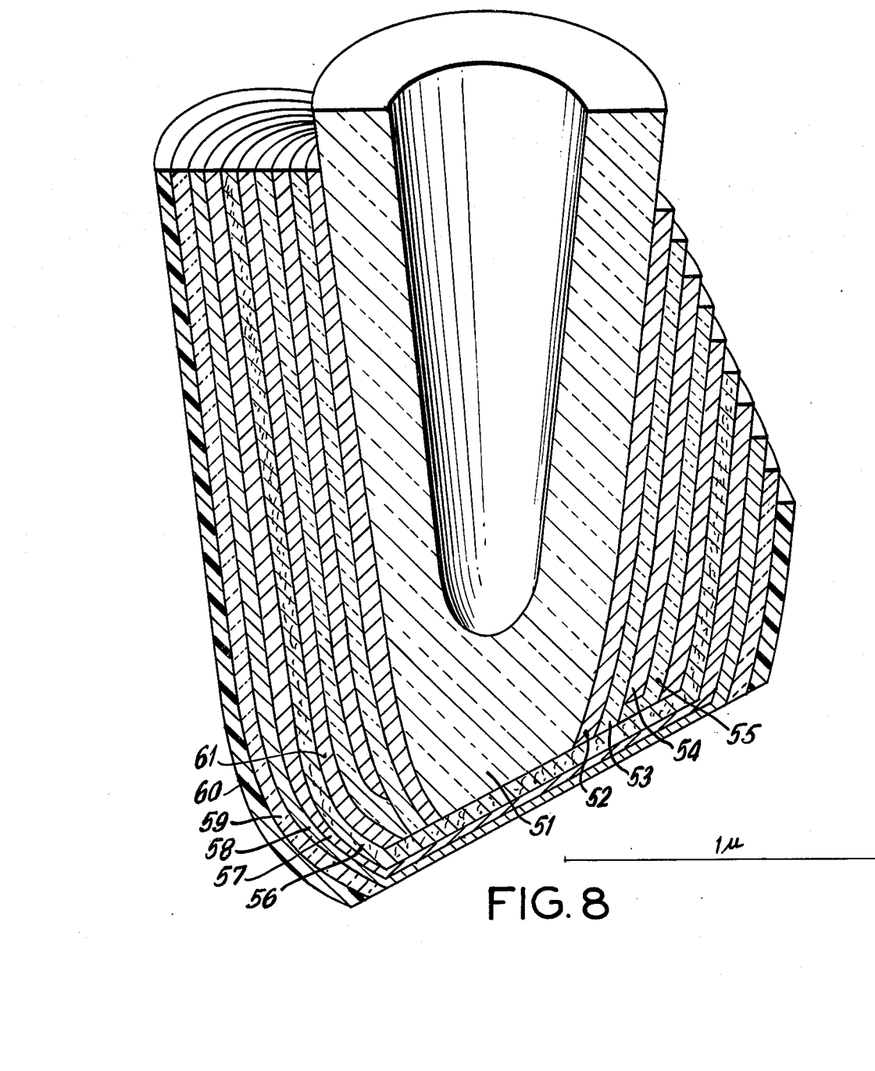
FIG. 8 is a sectional view of the tip of another embodiment of the inventive measuring probe comprising a reference electrode which extends over the measuring surface.

FIG. 8 shows a further embodiment of the probe tip which may be used in probes of the kind illustrated in FIGS. 2 or 6. In the illustrated design, this kind of tips is suitable for $pO_2$ impulse polarography. The relatively complicated stratification can be best explained in connection with the operational steps provided for its manufacture:

On a support tube 51, thinly drawn out and sealed at the end, an indicator electrode film 52 of gold and, thereon, an insulating sandwich film 53, are deposited. Onto film 53, a shielding film 54, again of gold, is applied while masking the area of the tip proper of the probe or, if very large probes are concerned, while screening this area, so that the shielding film does not extend up to the zone of the measuring surface to be provided later. Onto shielding film 54 and, in the tip zone, onto insulating film 53, another insulating film 55 is deposited, preferably also as a sandwich structure.

Thereupon, by cutting, grinding, ion beam removal, or the like, an effective surface extending substantially perpendicularly to the axis of the probe and across the hitherto deposited layers 52 to 54 and support 51 is produced into which layers 52, 53, 55 open. To the arrangement thus obtained, including the effective surface, a diaphragm 56 is applied, for example, by immersion. Thereupon, to the diaphragm enclosing the measuring surface, there is applied a reference electrode comprising an inside silver layer 57 and an outside gold layer 58. An insulating layer 59 and a layer 60 of waterproof material, serving as a water barrier, are also applied in the shank zone of the probe tip. Care must be taken not to cover the reference electrode layer 58, in the area of the effective surface, with the "TEFLON" layer 60 or insulating layer 59.

In this embodiment, shielding electrode layer 54 could also be designed as an aluminum or silicon layer which is oxidized in its portion adjacent the measuring surface. The embodiment of FIG. 8 differs from the embodiments hitherto discussed substantially in that its diaphragm 56 is not in contact with the medium to be measured surrounding the probe tip. In this embodiment, the diaphragm is, instead, covered by reference electrode layers 57 and 58. Since, however, with their chosen thickness in the range below 0.1μ, these reference electrode layers are extremely permeable, the penetration of oxygen and water to the diaphragm, covering the area of the effective surface, is assured. Thus, the diaphragm area covering the effective surface provides an all around closed electrolyte chamber which is shielded toward the measured medium, against disturbing ions, and in which the measuring process between the indicator and the reference electrode can take place without trouble.

Figure 9:
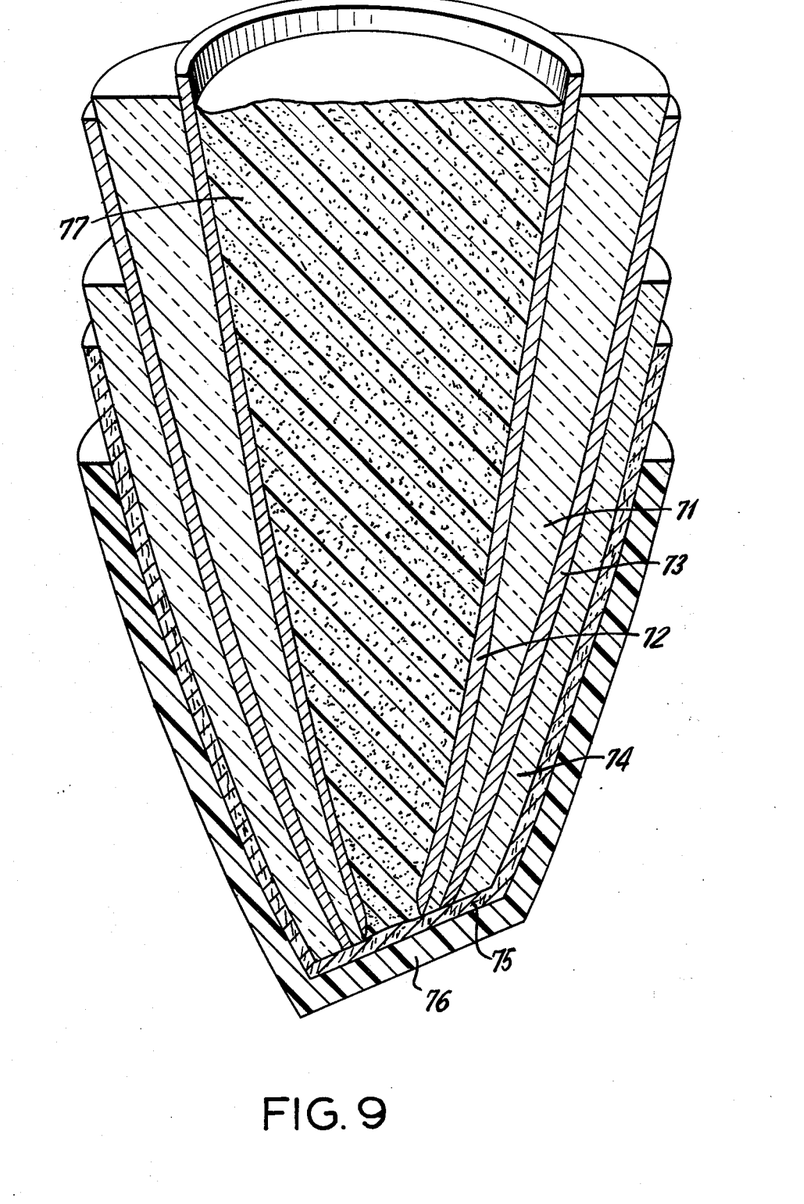
FIG. 9 is a sectional view of the tip of an inventive measuring probe of the Clark type.

FIG. 9 shows an embodiment of the inventive probe corresponding to the so-called "Clark" type. A support tube 71 having an open tip carries, on its interior surface, a reference electrode layer 72 and, on its exterior surface, an indicator electrode layer 73. For insulating indicator electrode layer 73, a thick insulating film 74 is provided in this case and advantageously may be designed as a sandwich structure. Tube 71, indicator electrode film 73 and insulating film 74 are cut off along the effective surface and coated with a diaphragm, similar to diaphragm 75 of FIG. 1, covering the probe tip and the aperture of the support tube. In addition, the diaphragm is covered with a plastic layer 76 impermeable to water, for example, of "TEFLON." The interior of the support tube is filled with an electrolyte 77. The rear or outer end of the probe may be designed in accordance with one of the embodiments already described, it being necessary only to provide a possibility of filling the interior of the probe with the electrolyte.

This probe operates in a manner similar to that of the probe of FIG. 8, i.e., without a direct contact of diaphragm 75 with the ambient medium since, in this case again, the diaphragm is covered with a "Teflon" layer which is impermeable to water. In the embodiment of FIG. 9, the electrolytic connection between the indicator electrode and the reference electrode is assured by diaphragm 75, which is permeable to water and ion conducting, and which is placed between the effective surface of the indicator electrode and the electrolyte space. Due to the fact that diaphragm 75 and layer 76 are firmly applied against the measuring surface, variations of geometry between the effective surface of indicator electrode 73 and that of the diaphragm which, in known probes of the Clark type, result in variations of the measured value caused by the variation of the resistance polarization and of the oxygen diffusion path, are eliminated. In the inventive Clark type probe according to FIG. 9, the oxygen diffusion path is permanently determined only by the layer thicknesses of diaphragm 75 and "Teflon" layer 76, while the resistance polarization is substantially determined by the also constant thickness of diaphragm 75. In addition, in this construction, the resistance polarization is negligible since the effective surface is very small and, moreover, distributed over a ring around the electrolyte space so that the current path extending through diaphragm 75, between the effective surface of the indicator electrode and the electrolyte space, is very extensive relative to the effective surface.

In a modified embodiment, the inventive Clark type probe may be designed also with a silver tube as the reference electrode, which is insulated to the outside and coated with outer layers having a structure in accordance with FIG. 9.

Figure 10:
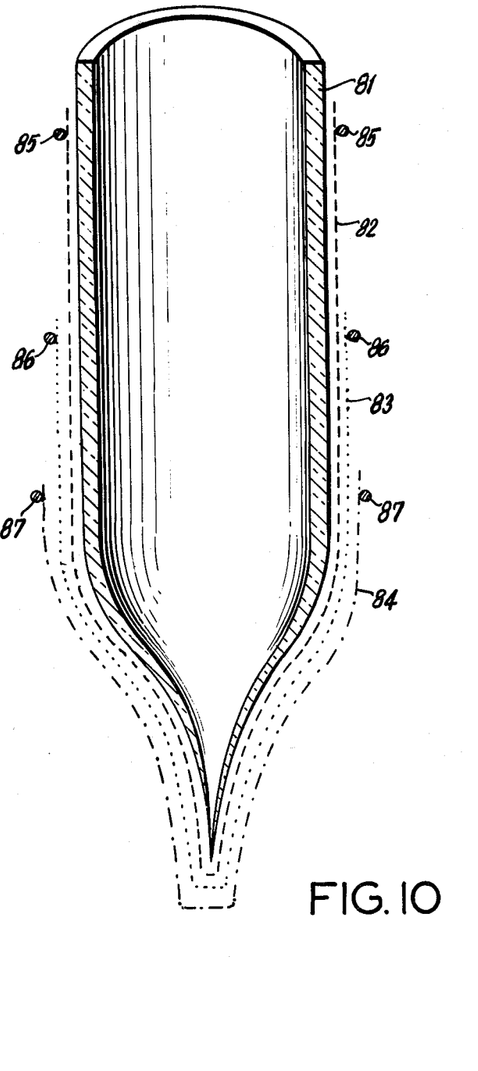
FIG. 10 is a sectional view of another embodiment of the inventive probe comprising only one support and three electrodes which are contacted with each other in a particular manner.

FIG. 10 shows another embodiment of the probe which is particularly small and, in spite of this, simple in manufacture and which may be used with a varying structure of the layers and with different designs of the tip. In contrast to the embodiment of FIG. 2, this probe comprises a single support tube 81 which, in the illustrated example, is drawn out to a thin probe tip. Onto this single support tube, all the layers are applied. In the diagrammatical illustration of FIG. 10, only the layers of indicator electrode 82, shielding electrode 83 and reference electrode 84 are indicated. Between the electrode layers, insulating layers and, if desired, additional waterproof layers (not shown) are provided. In contradistinction to the embodiment of FIG. 2, the layers are contacted with respective connecting wires 85, 86 and 87 which are not on different supports but on one and the same support. In this embodiment, each of the respective points of contact of the connecting wires is located on a respective non-insulated ring of the electrode surrounding support tube 81 and left bare during the application of the next layers, by using masks or screens. Consequently, the connecting wires may be secured after the deposition of all layers, by means of a conducting adhesive which has been appropriately pretreated.

Because of its very large electrode surfaces to be insulated from each other, the particularly simple embodiment of the probe in accordance with FIG. 10 is affected with quite insufficient insulating properties. A measuring of the extremely small currents resulting from the minimized effective surface of the indicator electrode is possible only in the "shifting shield" process which completely eliminates leak currents to the indicator electrode.

Figures 11, 12:
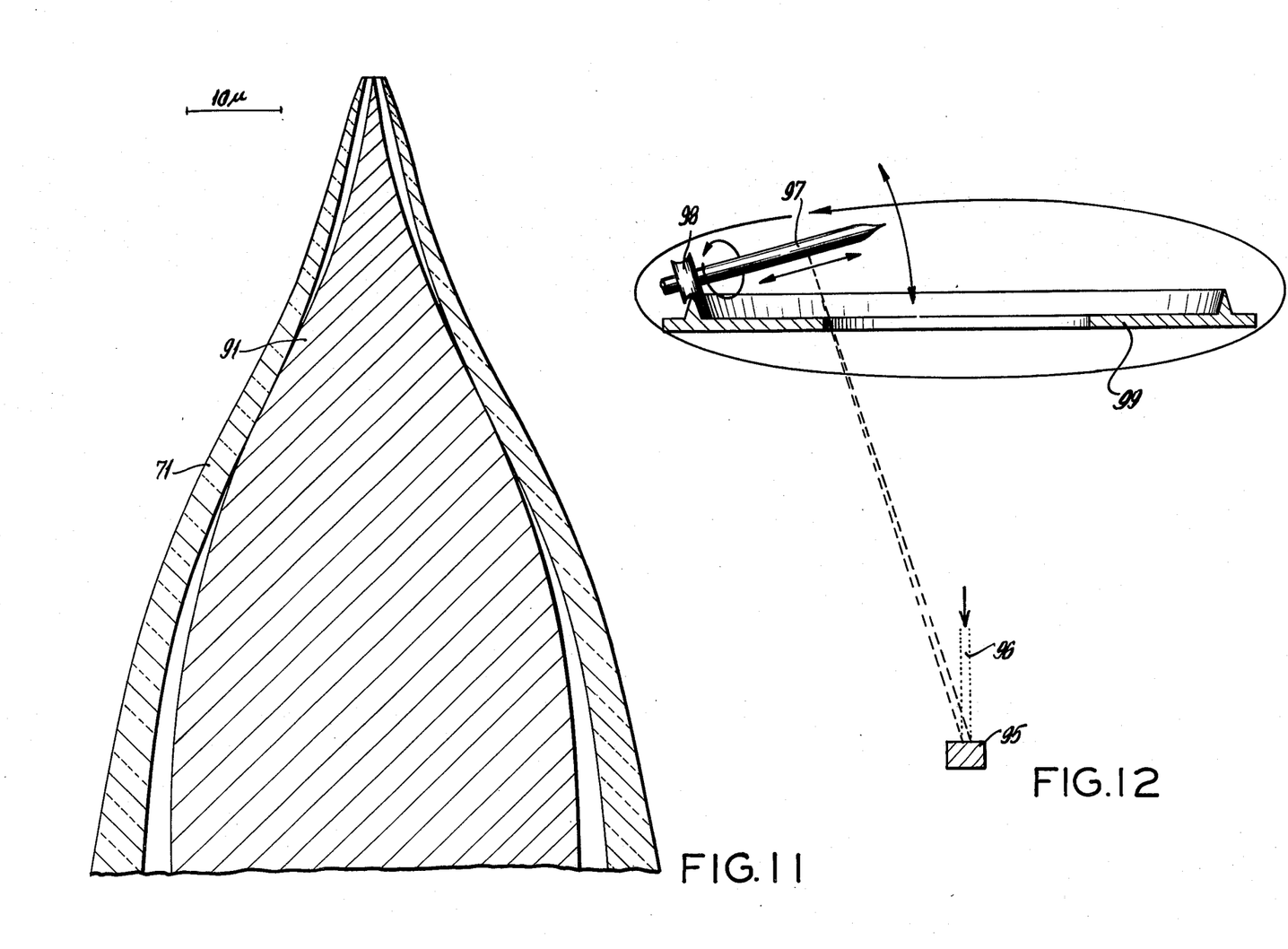
FIG. 11 is a sectional view of the tip of a tube accommodating a sputtering cathode for coating the inside of the tube in accordance with the invention.
FIG. 12 is a diagrammatical view of an arrangement for the outside coating of thin glass supports, in accordance with the invention.

FIG. 11 shows an arrangement for depositing the reference-electrode layer 72 which is made, for example, of silver, on the inside of support tube 71 in accordance with the embodiment of FIG. 9. According to the inventive method, a silver pin 91 which has been provided by etching or the like with a pointed front end portion whose radius decreases in the direction of the point slightly more than the inside radius of tube 71, is placed, with its point in the zone of the front aperture of tube 71, within the tube. Thereby, an interspace, widening in the direction of the front aperture of the tube or of the point of the pin, is formed between the surface of silver pin 91 and the inside surface of tube 71, into which interspace ions can penetrate from the tube aperture. The penetrating ions effect a cathode sputtering of the surface of silver pin 91 up to a zone which is relatively remote from the point. This arrangement assures a quite satisfactory coating of the inside of the tube up to relatively large distances from the front aperture of the tube, which coating cannot be obtained with conventional methods.

As may be seen in FIG. 11, silver pin 91 and tube 71 contact each other in a zone which is remote from the point. The silver layer is deposited on the inside surface of the tube only in the area up to this zone. To be sure, in the arrangement of FIG. 9, the reference electrode 72 is needed only in the foremost zone of the tube since, farther behind, the electrolyte cross-sectional area is large enough to carry the polarization current alone, without a too large resistance polarization.

FIG. 12 illustrates an arrangement for coating supports by cathode sputtering. A well focused ion beam 96 impinges, in a focal spot, on a target 95 which, depending on the layer to be deposited, is made of platinum, gold, silicon, or the like. Advantageously, the target is placed for replacement on a revolver or the like (not shown), along with other target materials needed for other layers.

From the focal spot of the ion beam on target 95, the target atoms or molecules knocked loose fly along straight paths, which, in FIG. 12, are indicated in broken lines, in all directions. An annular disc 99, having an inner rim, is fixedly mounted concentric with ion beams 96, and a wheel 98 is provided running on a rail which is also concentrically secured to disc 99.

By means of a drive and supporting device (not shown), wheel 98, the axis of which extends in the direction of ion beam 96, is rotated about its axis for running on the rail. The angle the wheel axis forms with ion beam 96 is adjustable, as indicated in FIG. 12.

Aligned with the axis of wheel 98, a support tube 97 is held in position and is displaceable in the axial direction. During the circulation of wheel 98 about ion beam 96, the end portion, facing the ion beam, of support 97 is coated up to a limit which is defined by the screen effect of the inner rim of annular disc 99. The limit up to which support tube 97 is coated is determined in that support tube 97 is displaced axially along the axis of wheel 98. The rate of coating can be chosen by angular adjustment of wheel 98, thus by angular adjustment of support 97 relative to the direction of impingement of the atoms.

The displacement in the axial direction, i.e., the adjustment of the coating limit, is important for the embodiment of the probe in accordance with FIG. 10, while the angular adjustment in the direction of the respective arrow is particularly important for producing the electrode layers in the embodiment of FIG. 8. With a support 97 in a downwardly directed oblique position, within the same period of coating time, reference-electrode layers having different thicknesses may be applied simultaneously to the tube in the zone of the measuring surface and in the shank zone.

The rotation of support tube 97 about its own axis obtained by the run of wheel 98 on the rail results in a uniform layer thickness round the support. The circulation of wheel 98 about ion beam 96 results in a uniform rate of coating since assymmetries in the angular distribution of the atoms knocked out from the target are compensated.

Support 97 may be held in position and driven also in another manner. It is important only to assure adjustment possibilities in the axial and swinging directions as well as the rotation of the support about its own axis and circulation around ion beam 96.

If a plurality of wheels 98 is provided, which may run on the same rail, the device in accordance with FIG. 12 is suited for a simultaneous treatment of a plurality of supports 97.

While specific embodiments of the invention have been shown and described in detail to illustrate the application of the principles of the invention, it will be understood that the invention may be embodied otherwise without departing from such principles.

What is claimed is:

1. In a measuring probe for polarographic determination of partial gas pressures, particularly partial pressures of oxygen in aqueous solutions, particularly in biological media, of the type having an indicator electrode which, except for a very small effective surface, is insulated all around, and a diaphragm protecting the effective surface against poisoning, and which probe has a reference electrode, the improvement comprising, in combination, insulating support means; said indicator electrode being constituted by a thin film of metal, having the properties of a noble metal, deposited on said insulating support means; a thin film insulating layer deposited on and covering said indicator electrode film; said effective surface being an exposed edge surface of said indicator electrode film forming part of a measuring surface of said probe, which measuring surface lies in a plane substantially perpendicular to the plane of said indicator electrode; a shielding layer, in the form of a thin film deposited on and covering the thin film insulating layer which insulates said indicator electrode; said shielding layer extending to at least adjacent said measuring surface; and means insulating said shielding layer from the exterior of said probe and from said measuring surface.

2. In a measuring probe, the improvement claimed in claim 1, including a reference electrode on the support constituted by a thin metal film deposited on said means insulating said shielding layer from the exterior of said probe; said insulating support means comprising a plurality of insulating supports carrying the respective electrodes and layers, the plurality of insulating supports each spaced laterally from each other by distances increasing in the direction of a connection zone of said probe spaced longitudinally from said measuring surface.

3. In a measuring probe, the improvement claimed in claim 2, in which said plurality of supports comprises concentric tubes tapering laterally inwardly in the direction of the tip of said probe; means securing said tubes, in the zone of said tip, to the respective underlying electrodes and layers; and means, in said connection zone, securing said tubes to each other.

4. In a measuring probe for polarographic detection of the partial pressure of oxygen in an aqueous solution, particularly in biological media, of the type having an indicator electrode which, except for a very small effective surface, is insulated all around, and a diaphragm protecting the effective surface against poisoning, and which probe has a reference electrode, the improvement comprising, in combination, insulating support means; said indicator electrode being constituted by a thin film of metal, having the properties of a noble metal, deposited on said insulating support means; a thin film insulating layer deposited on and covering said indicator electrode film; said effective surface being an exposed edge surface of said indicator electrode film forming part of a measuring surface of said probe, which measuring surface lies in a plane substantially perpendicular to the plane of said indicator electrode; a shielding layer, in the form of a thin film deposited on and covering the thin film insulating layer which insulates said indicator electrode; said shielding layer extending to at least adjacent said measuring surface and having an edge adjacent said measuring surface; and means insulating said shielding layer from the exterior of said probe and from said measuring surface; said shielding layer being selected from the group consisting of aluminum and silicon; said means insulating said shielding layer from said measuring surface comprising an oxide of said shielding layer extending along said edge of said shielding layer adjacent said measuring surface and disposed between said shielding layer and said measuring surface.

* * * * *